United States Patent [19]

Büchi et al.

[11] 4,346,023
[45] Aug. 24, 1982

[54] PROCESS FOR THE PREPARATION OF NOVEL UNSATURATED MACROCYCLIC KETONES

[75] Inventors: George H. Büchi; Hans Wüest, both of Cambridge, Mass.

[73] Assignee: Firmenich SA, Geneva, Switzerland

[21] Appl. No.: 244,629

[22] Filed: Mar. 17, 1981

Related U.S. Application Data

[60] Division of Ser. No. 76,960, Sep. 19, 1979, Pat. No. 4,302,607, which is a continuation-in-part of Ser. No. 11,685, Feb. 12, 1979, abandoned.

[51] Int. Cl.³ .................... A61K 7/46; C07C 49/547
[52] U.S. Cl. ............................. 252/522 R; 568/325; 426/534
[58] Field of Search .................. 568/375; 252/522 R

[56] References Cited

U.S. PATENT DOCUMENTS

| | | | |
|---|---|---|---|
| 3,681,396 | 8/1972 | Mookherjee et al. | 568/375 |
| 3,923,699 | 12/1975 | Komatsu et al. | 568/375 |
| 4,277,625 | 7/1981 | Schulte-Elte et al. | 568/375 |

FOREIGN PATENT DOCUMENTS

| | | | |
|---|---|---|---|
| 119620 | 4/1927 | Switzerland | 568/375 |
| 119621 | 4/1927 | Switzerland | 568/375 |
| 1036084 | 7/1966 | United Kingdom | 568/375 |

*Primary Examiner*—Natalie Trousof
*Assistant Examiner*—James H. Reamer
*Attorney, Agent, or Firm*—Pennie & Edmonds

[57] ABSTRACT

New unsaturated macrocyclic ketones are obtained via a process which consists in reacting a dialdehyde with a tetraalkyldiphosphonate ester. The new ketones are useful intermediates for the preparation of cyclopentadecanone and its higher methyl-homologue, known fragrant substances. New ketones possess also direct utility as musky odorants.

9 Claims, No Drawings

PROCESS FOR THE PREPARATION OF NOVEL UNSATURATED MACROCYCLIC KETONES

This is a division, of application Ser. No. 076,960, filed Sept. 19, 1979 now U.S. Pat. No. 4,302,607 which in turn is a continuation in part of application Ser. No. 011,685, filed Feb. 12, 1979 and now abandoned.

BRIEF SUMMARY OF THE INVENTION

The invention relates to the field of perfumery, in particular it provides a process for the preparation of unsaturated macrocyclic ketones, which compounds found a utility as intermediate for the preparation of cyclopentadecanone ("EXALTONE®") and 3-methyl-cyclopentadecanone ("muscone"). The new macrocyclic ketones possess formula

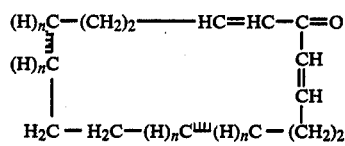

possessing two single or two double bonds in the positions indicated by the dotted lines and wherein index n stands for integer 1 or 2.

BACKGROUND OF THE INVENTION

Among the most appreciated musky ingredients known in the art of perfumery, certain macrocyclic ketones such as cyclopentadecanone and its higher methyl homologue, 3-methyl-cyclopentadecanone, better known under the name of EXALTONE® and muscone, respectively, have acquired a special renown.

A great number of synthetic methods have been proposed in the past for their preparation and a few of them have been applied for industrial production. In spite of this, owing to their high prices these macrocyclic ketones have found a rather limited utilization and industry has constantly spent a great deal of efforts for devising more economical processes for their preparation [see e.g. the review in Cosmetics and Perfumery, 88, 67 (1973)].

The present invention provides a new and original solution to this problem.

THE INVENTION

It is an object of the present invention to provide a process for the preparation of unsaturated macrocyclic ketones of formula

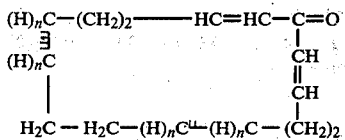

possessing two single or two double bonds in the positions indicated by the dotted lines and wherein index n stands for integer 1 or 2, which process comprises reacting in the presence of a basic reagent a dialdehyde of formula

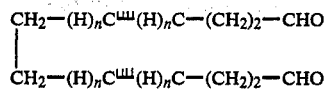

wherein the dotted lines and index n have the above given meaning, with a diphosphonate of formula

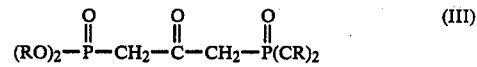

wherein each of symbols R represents an alkyl radical.

It has been surprisingly found that compounds (I) not only are useful intermediates for the preparation of cyclopentadecanone and 3-methyl-cyclopentadecanone, but that they represent useful perfume ingredients on their own right.

Due to the presence of several olefinic double bonds in their molecule, compounds (I) can occur under the form of stereoisomers of different configuration. Depending upon the nature of starting dialdehyde (II), compounds (I), as prepared in accordance with the process of the invention, can occur under the form of isomerically pure compounds or as mixture of two or more different isomers.

As indicated above symbols R in formula (III) represents alkyl radicals, preferably they stand for lower radicals, e.g. methyl or ethyl. Compounds (III) can be obtained according to partially known synthetic methods, for instance in accordance with the method illustrated hereinbelow:

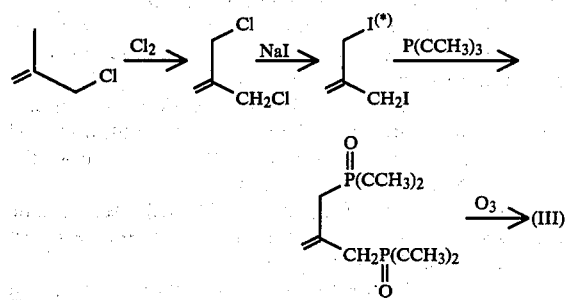

(*)see J. Amer. Chem. Soc., 89, 4688 (1967).

Dialdehydes (II), used as starting material in the process of the invention, can be prepared by mono-ozonisation of the corresponding cyclic olefine, viz. cyclododecene or cyclododecatriene, according to known methods [see e.g.: Swiss Patent No. 577'445 and Japanese Patent No. 75 03292].

The reaction between dialkyl-diphosphonate (III) and dialdehyde (II) occurs, according to the invention, in the presence of a basic reagent. Useful basic reagents include organic or mineral bases. Good yields of final products are obtained by using an alkali metal hydride, carbonate or bicarbonate; sodium hydride or potassium bicarbonate are preferred. The reaction is preferably carried out in an inert organic solvent, or aqueous organic solvent, such as an alcohol, e.g. ter-butanol, or an ether such as tetrahydrofuran or diethylene glycol dimethyl ether.

The said reaction can be effected either in a single step or as a combined two-step synthesis. In this latter case the first step consists in the formation of a monophosphonate which is then converted into the desired ketone by means of a further treatment with a basic reagent. This variant of the process of the invention is illustrated below:

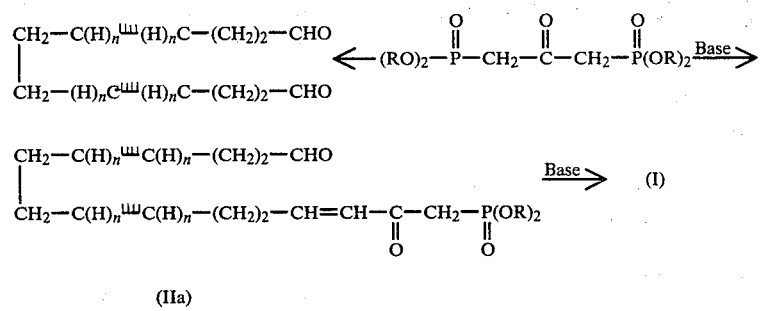

(IIa)

Though the temperature does not play any major determinant role for the good course of the reaction, it has been found that for economical and practical reasons a temperature of between about 50° and 100° C. can be satisfactorily applied. In this range of temperatures the formation of by-products is substantially reduced and the reaction times are sufficiently short.

On the contrary, when the process of the invention is carried out according to the two step variant described above, the temperature applied to the first reaction step is lower than the limit indicated.

Preferably, it is of about 20°–30° C., whereas the subsequent conversion is effected at a temperature of between about 50° and 100° C.

Compounds (I) are useful intermediates for the economical preparation of known EXALTONE® and muscone. The process which allows this conversion is illustrated hereinbelow:

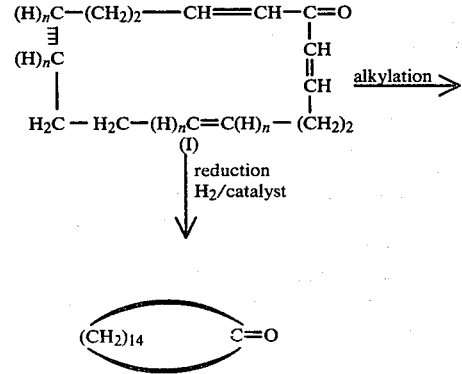

"EXALTONE®"

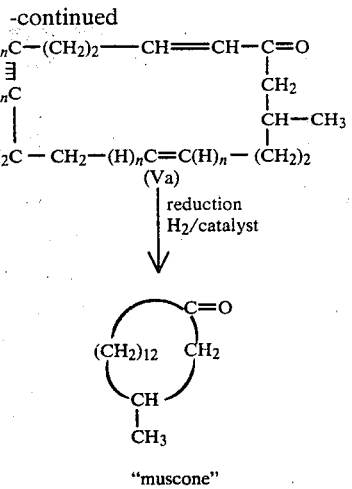

"muscone"

The alkylation of compounds (I) is effected according to usual techniques. Preferably it is promoted by means of organo-copper derivatives such as dimethyl-copper-lithium. The subsequent reduction is carried out by catalytic hydrogenation, e.g. in the presence of palladium on charcoal.

It is an object of the present invention to provide a process for the preparation of the macrocyclic ketones of formula

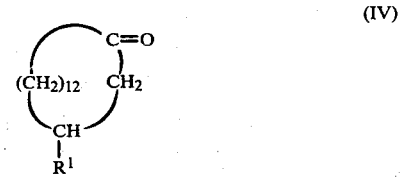

(IV)

wherein $R^1$ represents a lower alkyl radical or a hydrogen atom, which comprises a. reacting in the presence of a basic reagent a dialdehyde of formula

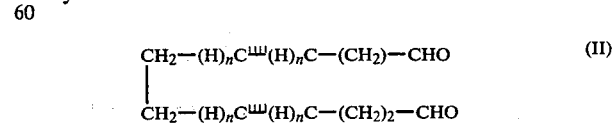

(II)

possessing two single or double bonds in the positions indicated by the dotted lines and wherein index n stands for integer 1 or 2, with a diphosphonate of formula $$(RO)_2-\overset{O}{\underset{\|}{P}}-CH_2-\overset{O}{\underset{\|}{C}}-CH_2-\overset{O}{\underset{\|}{P}}(OR)_2 \quad (III)$$

wherein each of symbols R represents an alkyl radical, to give an unsaturated macrocyclic ketone of formula $$\begin{array}{c}(H)_nC-(CH_2)_2\text{———}HC=HC-C=O\\ \underset{\underset{\displaystyle (H)_nC}{|}}{\|}\phantom{XXXXXXXXXXX}\underset{\underset{\displaystyle CH}{\|}}{CH}\\ |\phantom{XXXXXXXXXXXXXXXXXX}|\\ H_2C-H_2C-(H)_nC-(H)_nC-(CH_2)_2\end{array} \quad (I)$$

b. catalytically hydrogenating the thus obtained ketone to give cyclopentadecanone, or c. alkylating the ketone obtained sub. letter a. in order to obtain the compound of formula $$\begin{array}{c}(H)_nC\text{——}(CH_2)_2\text{——}CH=CH\text{——}C=O\\ \underset{\underset{\displaystyle (H)_nC}{|}}{\|}\phantom{XXXXXXXXXX}\underset{\underset{\displaystyle CH-R^1}{|}}{CH_2}\\ |\phantom{XXXXXXXXXXXXXXXXX}|\\ H_2C-CH_2C-(H)_{\overline{n}}C(H)_{\overline{n}}-(CH_2)_2\end{array} \quad (V)$$

wherein $R^1$ represents a lower alkyl radical and index n has the above given meaning and d. catalytically hydrogenating compound (V) to give an alkylated macrocyclic ketone of formula $$\underset{\displaystyle R^1}{\underset{|}{(CH_2)_{12}\underset{\displaystyle CH}{\overset{\displaystyle C=O}{\diagup\!\!\!\diagdown}}CH_2}} \quad (IVb)$$

wherein $R^1$ has the above given meaning.

Symbol $R^1$ can designate a lower alkyl containing 1 to 3 carbon atoms, preferably it stands for methyl, ethyl or n-propyl, more preferably for a methyl radical.

As stated above, compounds (I) possess interesting odorous properties and consequently they find also an industrial utility as perfuming ingredients. Typically, they develop musky and animal fragrances of elegant and natural character and can find a utility for both fine perfumes and technical applications. The new compounds of formula (I) include cyclopentadeca-2,5,10,14-tetraen-1-one which compound develops the most prominent musky notes and consequently can find a preferred utilization. It will be appreciated by those skilled in the art that the useful compounds of formula (I) can be used at concentrations varying within a wide range of values, depending on the materials it is desired to perfume and the specific effect it is desired to achieve. For instance, we have observed that concentrations as low as 0.1% (by weight) can already produce odorous effects in perfume compositions; this value however can be as high as 3 or 5%, or even higher.

The compounds of formula (I) can be used as such in their isolated form or in admixture with other perfuming coingredients, diluents or carriers.

Compounds (I) can find a useful application also in the field of aromas. They develop fatty, green-earthy and animal gustative notes associated with musky characters. A preferred concentration range in these instances is of about 0.05 to 10 parts per million (ppm) by weight based on the weight of the flavoured material.

Their utilization as flavour modifier or flavour enhancer is very broad, compounds (I) can in fact be used to flavour foodstuffs in general, beverages and tobacco products.

An object of the present invention is also to provide a process for the preparation of an unsaturated macrocyclic ketone of formula $$\begin{array}{c}(CH_2)_5-CH=CH\\ |\phantom{XXXXXXXX}|\\ \underset{\underset{\displaystyle C}{\|}}{C}\phantom{XXXXXXXX}C=O\\ |\phantom{XXXXXXXX}|\\ (CH_2)_5-CH=CH\end{array}$$

which process comprises reacting in the presence of a basic reagent a dialdehyde of formula $$\begin{array}{c}(CH_2)_5-CHO\\ |\\ \underset{\underset{\displaystyle C}{\|}}{C}\\ |\\ (CH_2)_5-CHO\end{array}$$

with a diphosphonate of formula $$(RO)_2-\overset{O}{\underset{\|}{P}}-CH_2-\overset{O}{\underset{\|}{C}}-CH_2-\overset{O}{\underset{\|}{P}}(OR)_2 \quad (III)$$

The specific reaction conditions applied to the above described process are identical to those applied in the process previously described for the preparation of the new macrocyclic ketones of formula (I).

The above described dienynone is a useful starting material for the preparation of civetone a well known perfumery ingredient.

Its conversion into civetone can be effected by means of a catalytic hydrogenation, particularly in the presence of Pd/BaSO$_4$.

The invention is better illustrated by but not limited to the following examples wherein the temperatures are indicated in degrees centigrade and the abbreviations have the meaning common in the art.

EXAMPLE 1

Cyclopentadeca-2,6,10,14-tetraen-1-one

A 500 ml round bottom flask equipped with a magnetic stirrer, reflux condenser and gas inlet tube was charged with 4 g of potassium bicarbonate and 125 ml of aqueous 90% t-butanol. The stirred mixture was heated at vigorous reflux under a steady flow of argon, while a solution of 3.10 g (16 mMole) of dodeca-4,8-diene-1,12-dial and 4.40 g (16 mMole) of 1,3-bis(dimethylphosphoro)propan-2-one in 25 ml of 90% aqueous t-butanol was added at a constant rate over a period of 4 h. The reaction mixture was poured into water containing some sodium chloride, to avoid emulsions, extracted with ether, washed with brine, dried over sodium sulphate and evaporated. Distillation of the remaining oil gave 2.15 g (62%) of the desired tetraenone, b.p. 101°–105°/0.05 Torr. A sample was purified by chromatography on silica gel and showed m.p. 30°–37°;

IR(CHCl$_3$): 1670, 1645, 1620, 985 cm$^{-1}$;
NMR(CCl$_4$): 2.0-2.5 (12H, m); 5.1-5.5 (4H, m); 5.8-5.9 (4H, m) δ ppm
MS: M$^+$=216 (6); m/e: 41 (100).

1,3-Bis(dimethylphosphono)-propan-2-one used as starting material in the hereinabove described process was prepared as follows:

a. 1,3-bis(dimethylphosphono)-2-methylene-propane 400 ml of trimethyl phosphite was placed into a 2-l flask equipped with an addition funnel, a gas inlet tube, and a Vigreux column with distilling head. The phosphite was heated at reflux, then a solution of 131 g (0.425 Mole) of 2-iodomethyl-3-iodopropene [see J.Amer.Chem.Soc., 89, 4688 (1967)] in 200 ml of benzene was added dropwise over a period of 2 h, followed by an additional 100 ml of trimethyl phosphite within 30 min. The reaction was run under nitrogen, and approx. 150 ml of distillate was allowed to collect. Distillation of the reaction mixture afforded 106 g (92%) of the title compound, b.p. 125°-7°/0.08 Torr;
IR(CHCl$_3$): 1650, 1250, 1050, 800 cm$^{-1}$;
NMR (CCl$_4$): 2.75 (4H, d, J=24 Hz); 3.65 (12 H, d, J=10 Hz); 5.00 (2H, t, J=5 Hz) δ ppm
MS: M$^+$=272 (6); m/e: 163 (100).

b. 1,3-bis(dimethylphosphono)-propan-2-one

A solution of 27.2 g (0.10 Mole) of the diphosphonate obtained according to letter a. above in 250 ml of methanol was ozonized at −10° to −20°. Trimethyl phosphite was then added dropwise at −10° (very exothermic), and the mixture was left overnight at room temperature. The solvent was removed in vacuo, and the residue was distilled to give 24.5 g (90%) of the title compound: b.p. 156°-8°/0.08 Torr;
IR(CHCl$_3$) 1720, 1250, 1050 cm$^{-1}$;
NMR (CDCl$_3$) 3.35 (4H, d, J=23 Hz); 3.75 (12H, d, J=11 Hz) δ ppm;
MS M$^+$=274 (5); m/e: 124 (100).

EXAMPLE 2

Cyclopentadeca-2,14-dien-1-one a. 15-(dimethyphosphono)-pentadec-12-en-14-on-1-al A solution of 5 g of potassium bicarbonate in 150 ml of water was added to a mixture of 8.22 g (30 mMole) of 1,3-bis(dimethylphosphono)propan-2-one and 5.94 g (80 mMole) of dodecan-1,12-dial in 150 ml of t-butanol. After 2½ h stirring at 27° under nitrogen water was added and the mixture was extracted with ether. The organic layer was separated, washed with brine, dried over sodium sulphate and evaporated. The residue was chromatographed on 150 g of silica gel. Hexane-ethyl acetate 1:1 eluted 2.68 g of unreacted dodecan-1,12-dial and ether eluted 4.38 g (42%, resp. 75% when based on recovered dial) of the title compound as a viscous oil.
IR(CHCl$_3$): 2740, 1730, 1700, 1670, 1630, 1250, 1050 and 980 cm$^{-1}$;
NMR(CCl$_4$): 1.1-1.8 (16H, m); 2.0-2.5 (4H, m); 3.05 (2H, d, J=22 Hz); 3.70 (6H, d, J=11 Hz); 6.12 (1H, d, J=16 Hz); 6.85 (1H, d of t, J=6.5 and 18 Hz); 9.55 (1H, t, J=1.5 Hz) δ ppm;
MS: M$^+$=346 (4); 41 (100).

The reaction was run under a steady flow of nitrogen. The reaction flask (250 ml) was charged with 2 g of potassium bicarbonate and 100 ml of 90% t-butanol, while the dilution flask (250 ml) was filled with 90% t-butanol. 15-(dimethylphosphono)-pentadec-12-en-14-on-1-al (2.0 g, 5.8 mMole) in 10 ml of 90% t-butanol was introduced within 4 h by means of a syringe pump, then refluxing was continued for 2 h. The reaction mixture was poured into water, extracted with pentane, washed with water, dried over sodium sulphate, and evaporated. Distillation of the residue gave 0.70 g (55%) of a ca. 9:1 isomeric mixture of cyclopentadeca-2,14-dien-1-one, b.p. 105°/0.1 Torr. Pure samples were obtained by chromatography on silica gel with hexane+5% ethyl acetate as eluant. Cyclopentadeca-2,14-dien-1-one (trans-trans isomer):
IR(CHCl$_3$): 1670, 1620, 980 cm$^{-1}$;
NMR(CCl$_4$): 1.2-1.7 (16H, m); 2.1-2.4 (4H, m); 6.15 (2H, d, J=17 Hz); 6.62 (d of t, J=17 and 6.5 Hz) δ ppm;
MS: M$^+$=220; m/e: 41 (100).

Cyclopentadeca-2,14-dien-1-one (cis-trans isomer):
IR(CHCl$_3$): 1660, 1620, 980 cm$^{-1}$;
NMR(CCl$_4$): 1.1-1.7 (16H, m); 2.1-2.5 (4H, m), 5.76 (1H, d of t, J=12 and 7 Hz); 6.10 (1H, d, J=15 Hz); 6.14 (1H, d, J=12 Hz); 6.75 (1H, d of t, J=15 and 7 Hz);
MS: M$^+$=220 (2); m/e: 41 (100).

8

The above reaction was repeated, but 15-(dimethylphosphono)-pentadec-12-en-14-on-1-al was replaced by a mixture of 0.79 g (4 mMole) of dodecan-1,12-dial and 1.10 g (4 mMole) of 1,3-bis(dimethylphosphono)-propan-2-one in 10 ml of 90% t-butanol. Identical introduction time and work up gave 229 mg (26%) of cyclopentadeca-2,14-dien-1-one in a similar ratio of isomers.

EXAMPLE 3

Conversion of cyclopentadeca-2,14-dien-1-one into EXALTONE ®

A solution of 1.00 g (4.55 mMole) of cyclopentadeca-2,14-dien-1-one in 20 ml of ethanol was hydrogenated in the presence of 50 mg of palladium on charcoal. Hydrogen uptake (230 ml) was complete after 1 h at 20°. The mixture was filtered, evaporated and distilled to give 0.96 g (94%) of EXALTONE ® having b.p. 115°/0.1 Torr; m.p. 65°-66°.

A mixture of EXALTONE ® and dehydro-EXALTONE ® could be obtained by direct conversion of 15-(dimethylphosphono)-pentadec-12-en-14-on-1-al as follows: The reaction was run under a steady flow of hydrogen. The 250 ml flask contained 2 g of potassium bicarbonate, 0.25 g of 10% palladium on charcoal, and 100 ml of 90% t-butanol and the dilution flask (100 ml) was filled with 90% t-butanol. 15-(Dimethylphosphono)-pentadec-12-en-14-on-1-al (0.75 g; 2.17 mMole) in 10 ml of 90% t-butanol was introduced over a period of 4 h and refluxing was continued for 2 h. Filtration of the reaction mixture, followed by usual work up gave 305 mg (63%) of a ca. 3:1 mixture of EXALTONE ® and dehydro-EXALTONE ® at b.p. ca. 120°/0.1 Torr. Separation was achieved by chromatography on silica gel with hexane/5% ethyl acetate. Dehydro-EXALTONE ® showed the following analytical data:
IR(CHCl$_3$): 1685, 1655, 1630 and 975 cm$^{-1}$;
NMR(CCl$_4$): 1.1-1.8 (20H, m); 2.1-2.6 (4H, m); 6.05 (1H, m, J=16 Hz); 6.65 (1H, d of t, J=16 and 7 Hz) δ ppm;
MS: M$^+$=222 (8); m/e: 41 (100).

EXAMPLE 4

Conversion of cyclopentadeca-2,14-dien-1-one into muscone a. 14-Methyl-cyclopentadec-2en-1-one (dehydromuscone)

To the Grignard reagent prepared from 72 mg (3 mg-atoms) of magnesium and 0.25 ml (4 mMole) of iodomethane in 5 ml of ether was added 50 mg of cuprous iodide, and the mixture was heated at reflux for 5 min. Cyclopentadeca-2,14-dien-1-one (0.44 g; 2 mMole) in 5 ml of ether was then added over a period of 10 min without cooling, and stirring was continued for 30 min at room temperature. The reaction mixture was poured into cold ammonium chloride solution and extracted with ether. The organic layer was washed with water, dried over sodium sulphate, evaporated and distilled to give 0.33 g (69%) of dehydromuscone having b.p. 110°/0.1 Torr;

IR(CHCl$_3$): 1680, 1655, 1615, 975 cm$^{-1}$;

NMR(CCl$_4$): 1.03 (3H, d, J=6 Hz); 1.1–1.7 (19H, m); 2.0–2.4 (4H, m); 6.07 (1H, d, J=16 Hz); 6.70 (1H, d of t, J=16 and 7 Hz) δ ppm;

MS: M$^+$=236 (8); m/e: 41 (100).

b. Muscone

A solution of 0.71 g (3 mMole) of dehydro-muscone in 20 ml of ethanol was hydrogenated in the presence of 50 mg of palladium on charcoal. Hydrogen absorption ceased after 45 min at 20° (74 ml). Filtration, evaporation and distillation yielded 0.66 g (92%) of muscone, b.p. 115°/0.1 Torr.

EXAMPLE 5

Conversion of cyclopenta-2,6,10,14-tetraen-1-one into EXALTONE ®

A solution of 0.89 g (4.1 mMole) of cyclopenta-2,6,10,14-tetraen-1-one in 20 ml ethanol was hydrogenated in the presence of 0.1 g of 10% palladium on charcoal (75 min, 20°, 750 Torr). Filtration, evaporation and distillation yielded 0.90 g (98%) of EXALTONE ® having b.p. 85°/0.05 Torr; m.p. 65°–7°.

EXAMPLE 6

Conversion of cyclopenta-2,6,10,14-tetraen-1-one into muscone a. 3-Methyl-cyclopenta-6,10,14-trien-1-one

To a stirred suspension of 0.86 g (4.5 mMole) of cuprous iodide in 25 ml of anhydrous ether was added 4.7 ml (9 mMole) of 1.9 M methyllithium in ether at −10° under argon. 0.89 g of cyclopenta-2,6,10,14-tetraen-1-one (4.1 mMole) in 10 ml of ether were then added at −10° over a period of 10 min and stirring was continued for 30 min at −10° to 0°. The reaction mixture was then poured into dilute, cold sulfuric acid, extracted with ether, washed with water, 5% sodium bicarbonate, and finally dried over sodium sulphate. Evaporation, followed by distillation afforded 0.77 g (81%) of the desired trienone having b.p. 95°–8°/0.05 Torr.

IR(CHCl$_3$): 1690, 1660, 1625 and 970 cm$^{-1}$;

NMR(CCl$_4$): 0.7–1.0 (3H); 1.1–2.9 (15H, m); 5.1–5.5 (4H, m); 5.9 (1H, d, J=17 Hz); 6.5 (1H, d of t, partially resolved) δ ppm;

MS: M$^+$=232 (1); m/e: 41 (100).

b. Muscone

A solution of 0.77 g (3.3 mMole) of the obtained trienone—see parag. a. above—in 20 ml of ethanol was hydrogenated in the presence of 0.1 g of 10% palladium on charcoal (1 h, 20°, 760 Torr). Filtration, evaporation and distillation gave 0.77g (98%) of muscone having b.p. 95°/0.05 Torr.

EXAMPLE 7

Civetone a. Cyclohepta-2,16-dien-9-yn-1-one

A solution of 4.44 g (20 mMole) of tetradec-7-yn-1,14-dial and 6.03 g (22 mMole) of 1,3-bis(dimethylphosphono)-propan-2-one (see Example 1) in 30 ml of a 9:1 mixture of t-butanol and water was added to a refluxing mixture of 5 g (50 mMole) of KHCO$_3$ and 200 ml of the 9:1 mixture of t-butanol and water over a period of 1½ h. After addition of water the mixture was extracted with ether, washed with brine, dried over Na$_2$SO$_4$ and evaporated. Distillation of the residue gave 2.75 g (yield 56%) of cyclohepta-2,16-dien-9-yn-1-one at b.p. 128°/0.05 Torr. which solidified and was crystallized from hexane; m.p. 55°–6°.

IR: 1660, 1640, 1615, 980 cm$^{-1}$;

NMR: 1.3–1.9 (12 H, m); 2.0–2.6 (8H, m); 6.25 (2H, d, J=17); 6.80 (2H, d of t, J=17 and 6.5) δ ppm;

MS: M$^+$=244 (1); m/e: 41 (100).

UV: 240 mu (ε=15,100).

b. Conversion of the obtained ynone into civetone 2.60 g (10.6 mMole) of the ynone obtained sub letter a. above in 75 ml of pyridine was hydrogenated at 20°/760 Torr in the presence of 0.2 g of 5% Pd/BaSO$_4$ until absorption ceased (3.5 h). The mixture was filtered, evaporated and distilled to yield 2.64 g (yield 99%) of civetone, b.p. 103°/0.05 Torr;

IR: 1700 cm$^{-1}$;

Identity with authentic civetone was established by comparison of spectra and retention times on gas chromatography.

Tetradec-7-yn-1,14-dial, used as starting material in the above described process, can be prepared as follows:

i. 56 g (0.4 Mole) of cyclohexanone enolacetate in 500 ml of methanol was ozonised in a dry ice-acetone bath until the solution turned blue. 60 ml of dimethyl sulphide was added, and the cooling bath was removed. The temperature rose slowly to 48°, and after it had returned to room temperature, 40 ml of trimethyl orthoformate and 1 ml of acetyl chloride were added. The mixture was then left for 48 h at room temperature. Three identical batches were combined and the solvent was removed in vacuo. The residue was dissolved in ether, washed with brine containing a small amount of NaHCO$_3$, dried (Na$_2$SO$_4$), and distilled to give 193 g of product, b.p. 56°–69°/0.1 Torr. The NMR spectrum indicated the presence of ca. 20% of methyl 6-oxohexanoate. The product was mixed with 100 ml of trimethyl orthoformate, 20 ml of methanol, and 0.5 g of p-toluene sulfonic acid. The mixture was left for 48 h at room temperature, then worked up as above yielding 201 g (88%) of methyl 6,6-dimethoxyhexanoate. b.p. 61°/0.1 Torr.

ii. A solution of 201 g (1.06 Mole) of the product obtained sub i. in 500 ml of dry ether was added at reflux temperature within 1 h to a stirred suspension of 30 g (0.75 Mole) of LiAlH$_4$ in 750 ml of ether. Stirring was continued for 1 h at room temperature, then 100 ml of 5 N NaOH was added slowly with external cooling. Stirring became difficult, but improved toward the end. After completion of the addition stirring was continued for 1 h, then the suspension was suction filtered, washed with ether, and evaporated. Distillation afforded 169 g (98%) of 6,6-dimethoxy-1-hexanol, b.p. 78°/0.1 Torr.

iii. 81 g (0.5 Mole) of 6,6-dimethoxy-1-hexanal was added to an ice-cooled mixture of 99.3 g (0.52 Mole) of p-toluene-sulfonyl chloride and 72 ml (0.9 Mole) of pyridine at such a rate that the temperature remained below 15°. Stirring was continued for 2 h at 5°–10°, then cold water was added and the mixture was extracted with ether. The organic layer was washed with 5% aq. AcOH, cold 2% NaOH, dried (Na$_2$SO$_4$), and evaporated at 20°. The residue (190 g) was dissolved in 500 ml of acetone, then a solution of 97.5 g (0.65 Mole) of NaI in 500 ml of acetone was added, and the mixture was stirred for 24 h at room temperature. Most of the solvent was removed in vacuo, then ether was added. The mixture was washed with water, dried (Na$_2$SO$_4$), evaporated and distilled to give 124.9 g (92%) of 1,1-dimethoxy-6-iodohexane, b.p. 76°–78°/0.05 Torr.

iv. Acetylene was bubbled through ca. 300 ml of liquid ammonia while 8.1 g (0.35 atom) of sodium was added in small pieces. After the disappearance of the blue color, dimethylsulfoxide (150 ml) was added cautiously. 1,1-Dimethoxy-6-iodohexane (8.16 g; 0.3 Mole) was then added over a period of 10 min. while acetylene was bubbled through the stirred mixture. The ammonia was allowed to evaporate and was replaced with ether. When the mixture had reached 0°, dilute NH$_4$Cl solution was added. The organic layer was separated, washed with water, dried (Na$_2$SO$_4$), and evaporated. Distillation of the residue gave 48.9 g (96%) of 1,1-dimethoxy-oct-7-yne, b.p. 91°/8 Torr.

v. To a stirred suspension of lithium amide, prepared from 1.45 g (0.21 atom) of lithium in ca. 200 ml of liquid ammonia was added 30.6 g (0.18 Mole) of 1,1-dimethoxy-oct-7-yne over a period of 10 min. Dimethyl-sulfoxide (100 ml) was then added, followed by 62.5 g (0.23 Mole) of 1,1-dimethoxy-6-iodohexane within 10 min. Work-up as above gave an oil, from which low-boiling impurities were removed by heating at 100°/0.05 Torr. Crude tetradec-7-yn-1,14-dial dimethylacetal (40.8 g, 72% yield) was used without further purification. A sample was submitted to a rapid distillation: b.p. 140°/0.05 Torr.—IR: 1125, 1070, 1050 cm$^{-1}$.

NMR: 1.1–1.8 (16 H, m); 1.9–2.3 (4 H, m); 3.25 (12 H, s), 4.35 (2H, t, J=6) δ ppm.

vi. A mixture of 31.4 g (0.10 Mole) of the obtained diacetal, 300 ml of tetrahydrofuran, 100 ml of water, and 0.5 ml of 70% perchloric acid was stirred at room temperature under argon. After 8 h a further 75 ml of water was added, and stirring was continued overnight. The mixture was poured into water, extracted with ether, washed with brine containing Na$_2$CO$_3$, dried (Na$_2$SO$_4$), and evaporated. Distillation afforded 21.1 g (95%) of tetradec-7-yn-1,14-dial, b.p. 125°–127°/0.05 Torr.

IR: 2725, 1720 cm$^{-1}$.

NMR: 1.1–1.8 (12H, m); 1.9–2.6 (8H, m); 9.65 (2H, t, J=~2) δ ppm.

EXAMPLE 8

A base perfume composition was prepared by mixing together the following ingredients (parts by weight):

| | |
|---|---|
| Vetyveryl acetate | 200 |
| Synthetic lily-of-the-valley base | 150 |
| p-Methyl-phenylacetaldehyde 10%(*) | 140 |
| HEDIONE ®(**) | 80 |
| Phenylethanol | 70 |
| Synthetic rose base (WARDIA ®(**)) | 70 |
| Styrallyl acetate | 30 |
| Galbanum oil 10%(*) | 30 |
| Citronellol | 30 |
| Geranium oil | 30 |
| Synthetic orris oil 10%(*) | 30 |
| Lavender oil | 20 |
| Absolute oak-moss 50%(*) | 20 |
| Indol 10%(*) | 20 |
| Base CYCLOSIA ®(**) | 20 |
| Petitgrain Bigarade oil | 15 |
| Ylang-ylang oil | 15 |
| Lemon TETRAROME(**) | 10 |
| | 980 |

(*)in diethyl phthalate
(**)origin: Firmenich SA, Geneva, Switzerland

By adding to 98 g of the above base 2 g of cyclopentadeca-2,6,10,14-tetraen-1-one there was obtained a novel composition possessing a more elegant, and a richer and more tenacious fragrance.

EXAMPLE 9

0.1 g of a 0.1% solution of cyclopentadeca-2,6-10,14-tetraen-1-one in 95% ethanol were sprayed onto 100 g of a tobacco mixture of the "american blend" type. The tobacco thus flavoured was then used for the manufacture of "test" cigarettes the smoke of which was subjected to an organoleptic evaluation by a panel of flavour experts. These latter declared that the smoke of the test cigarettes presented a marked musky character when compared to the smoke of the "control" cigarettes the tobacco of which was simply treated with 95% ethanol.

What we claim is:

1. An unsaturated macrocyclic ketone of formula

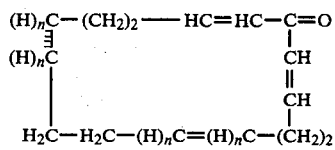

processing two single or two double bonds in the positions indicated by the dotted lines and wherein index n stands for integer 1 or 2.

2. Cyclopentadeca-2,6,10,14-tetraen-1-one.
3. Cyclopentadeca-2,14-dien-1-one.
4. A compound of formula

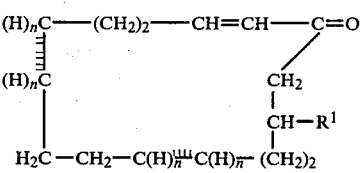

possessing two single or two double bonds in the positions indicated by the dotted lines and wherein R$^1$ represents a lower alkyl radical and index n stands for integer 1 or 2.

5. 3-Methyl-cyclopentadeca-6,10,14-trien-1-one.
6. 3-Methyl-cyclopentadec-14-en-1-one.

7. Method for improving, enhancing or modifying the olfactive properties of perfumes and perfumed products which comprises adding thereto a perfuming effective amount of a compound of formula (I) or of formula (V), as set forth in claim 1 or 4, respectively.

8. A perfume composition which comprises having added thereto a perfuming effective amount of a compound of formula (I) or of formula (V), as set forth in claim 1 or 4, respectively.

9. A flavour composition which comprises having added thereto a flavouring effective amount of a compound of formula (I) or of formula (V), as set forth in claim 1 or 4, respectively.

* * * * *